(12) United States Patent
Peterson

(10) Patent No.: US 9,200,890 B2
(45) Date of Patent: Dec. 1, 2015

(54) MACHINE VISION SYSTEMS AND METHODS WITH PREDICTIVE MOTION CONTROL

(75) Inventor: Dale Peterson, Waukesha, WI (US)

(73) Assignee: Cognex Corporation, Natick, MA (US)

( * ) Notice: Subject to any disclaimer, the term of this patent is extended or adjusted under 35 U.S.C. 154(b) by 494 days.

(21) Appl. No.: 13/477,861

(22) Filed: May 22, 2012

(65) Prior Publication Data

US 2013/0314530 A1 Nov. 28, 2013

(51) Int. Cl.
| | | |
|---|---|---|
| H04N 5/32 | (2006.01) | |
| G01B 11/04 | (2006.01) | |
| G01B 11/24 | (2006.01) | |
| H04N 5/232 | (2006.01) | |
| H04N 5/235 | (2006.01) | |
| G01N 21/88 | (2006.01) | |
| G03B 15/16 | (2006.01) | |

(52) U.S. Cl.
CPC ............ *G01B 11/04* (2013.01); *G01B 11/24* (2013.01); *G01N 21/8806* (2013.01); *H04N 5/232* (2013.01); *H04N 5/2353* (2013.01); *G03B 15/16* (2013.01); *H04N 5/23206* (2013.01)

(58) Field of Classification Search
None
See application file for complete search history.

(56) References Cited

U.S. PATENT DOCUMENTS

| | | | |
|---|---|---|---|
| 5,586,058 A | 12/1996 | Aloni et al. | |
| 5,940,296 A | 8/1999 | Meyer | |
| 6,167,148 A | 12/2000 | Calitz et al. | |
| 6,504,611 B2 | 1/2003 | Kogan et al. | |
| 6,610,991 B1 | 8/2003 | Case et al. | |
| 7,529,599 B1 * | 5/2009 | Bhatt et al. | 700/250 |
| 7,656,751 B2 * | 2/2010 | Rischar et al. | 368/46 |
| 7,760,238 B2 * | 7/2010 | Giesen | 348/211.3 |
| 7,791,671 B2 * | 9/2010 | Schultz et al. | 348/375 |
| 7,915,570 B2 | 3/2011 | Cetrulo et al. | |
| 8,145,338 B2 * | 3/2012 | Kent et al. | 700/110 |
| 8,687,060 B1 * | 4/2014 | Wolff | 348/140 |
| 2002/0177974 A1 | 11/2002 | Ting et al. | |
| 2008/0240321 A1 * | 10/2008 | Narus et al. | 375/356 |
| 2009/0144647 A1 * | 6/2009 | Chandhoke | 715/772 |

(Continued)

FOREIGN PATENT DOCUMENTS

| | | |
|---|---|---|
| CN | 101276218 | 10/2008 |
| JP | 04348050 | 12/1992 |

(Continued)

OTHER PUBLICATIONS

Harris, Ken. "An Application of IEEE 1588 to Industrial Automation." Article. Published by Rockwell Automation, Jan. 2009. pp. 1-6.

(Continued)

*Primary Examiner* — Sath V Perungavoor
*Assistant Examiner* — Janese Duley
(74) *Attorney, Agent, or Firm* — Quarles & Brady LLP

(57) ABSTRACT

Systems and methods trigger an image acquisition of an object using motion data communicated from a motion controller on a network, the motion controller coupled to a motion drive. A camera, upon receiving motion data from the motion controller, uses a virtual axis application to plan the movement of a virtual axis for a motion cycle, the virtual axis allowing an acquisition trigger rate to be calculated by the camera that follows movement of the object caused by the motion drive. Based on the calculated acquisition trigger rate, the camera generates an acquisition trigger signal for triggering the image acquisition of the object.

24 Claims, 4 Drawing Sheets

(56) References Cited

U.S. PATENT DOCUMENTS

| | | |
|---|---|---|
| 2010/0073665 A1 | 3/2010 | Zhao et al. |
| 2011/0141269 A1 | 6/2011 | Varga et al. |
| 2011/0199532 A1 | 8/2011 | Jin |
| 2011/0297590 A1* | 12/2011 | Ackley et al. .................. 209/580 |
| 2012/0150336 A1* | 6/2012 | Kent et al. ..................... 700/110 |

FOREIGN PATENT DOCUMENTS

| | | |
|---|---|---|
| JP | 2011124759 | 6/2011 |
| WO | WO2006021219 A1 | 3/2006 |
| WO | 2009021219 A2 | 2/2009 |

OTHER PUBLICATIONS

"ControlLogix Digital I/O Modules." User Manual. Published by Rockwell Automation, Aug. 2010. pp. 52-54.

"1732E ArmorBlock EtherNet/IP Dual Port 8-Point Sequence of Events Input and Scheduled Output Modules." User Manual. Published by Rockwell Automation, Feb. 2012. pp. 59-84.

* cited by examiner

MACHINE VISION SYSTEMS AND METHODS WITH PREDICTIVE MOTION CONTROL

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to vision systems, and more specifically, to a vision system coupled to a motion controller, the motion controller providing motion data used for generating an image acquisition trigger signal.

In many applications, machine vision or image processing analysis is used to inspect or locate an object. For example, in manufacturing applications, machine vision analysis may be used to detect defects in a manufactured object by acquiring images of the object and using various types of image processing algorithms to analyze the images. As an example, a system to manufacture an object such as a memory disk may use machine vision to examine the object in order to detect manufacturing defects, and ensure that the object is marked or assembled properly.

In such machine vision systems, an encoder is often used to communicate object position to the vision system in order to generate trigger signals at calculated times and to schedule the generation of digital outputs. The trigger signals are used to acquire one or more images of the object in the field of view as it moves in front of the vision system, and the digital outputs may be used for triggering a reject mechanism, for example. FIG. 1 shows an illustrative machine vision system 20 adapted to acquire one or more images 22 of a memory disk 24. Conveyor 28 transports the disks 24 to cause relative movement between the disks 24 and the field of view 30 of imaging device 32. Motion of the conveyer 28 is tracked by one or more encoders 36. The encoder 36 sends signals over link 40 to a processor 42, which uses the encoder signals to calculate disk position, and to generate a trigger signal over link 44 at calculated times to the imaging device 32 to acquire one or more images of the disk 24 in the field of view. If the disk 24 is defective, the imaging device 32 and/or the controller 42 may be programmed to send a signal over link 46 to a reject actuator 48 to remove the defective disk 50 from the conveyer 28 as shown.

However, encoders can be troublesome and undesirable due to their inaccuracies, noise immunity issues, and reliability issues. Removing the need for a separate encoder to provide position data to the imaging device would improve overall performance for the machine vision system, reduce points of failure, and increase efficiencies for the vision system user. What is needed are machine vision systems and methods that can calculate object position using motion data from a motion controller.

BRIEF SUMMARY OF THE INVENTION

The present embodiments overcomes the disadvantages of the prior art by calculating object position using motion data from a motion controller.

Accordingly, some embodiments comprise a vision system for triggering an image acquisition of an object using motion data communicated from a motion controller on a network, the motion controller coupled to a motion drive. The vision system comprises a camera, with an acquisition controller coupled to the camera, the acquisition controller including a network interface, and the network interface operable to couple to the network. The camera, upon receiving motion data from the motion controller, uses a virtual axis application to plan the movement of a virtual axis for a motion cycle, the virtual axis allowing an acquisition trigger rate to be calculated by the camera that follows movement of the object caused by the motion drive. And, based on the calculated acquisition trigger rate, the camera generates an acquisition trigger signal for triggering the image acquisition of the object.

Other embodiments comprise a vision system including a camera, the camera operable to trigger an image acquisition of an object using motion data communicated from a motion controller on a network, and the motion controller coupled to a motion drive. The camera includes a virtual axis application and an acquisition controller, the acquisition controller coupleable to the network. A common time reference is provided by at least one of the motion controller, a camera clock, a dedicated master clock, and the motion drive. The camera, upon receiving the motion data communicated from the motion controller, uses a virtual axis application to plan the movement of a virtual axis for a motion cycle, the virtual axis operable to follow relative movement of the object caused by the motion drive. And, based on movement of the virtual axis, the camera generates an acquisition trigger signal for triggering the image acquisition of the object.

Consistent with the above, some embodiments include a method for acquiring an image. The method comprises providing a common time reference to a camera and a motion controller, the camera and the motion controller being in communication on a network; the motion controller sending motion data to a motion drive; the motion controller sending the motion data over the network to the camera; upon receiving the motion data, the camera planning the movement of a virtual axis, the virtual axis moving in a fixed relationship to the motion drive; using the virtual axis, generating an image acquisition trigger rate that virtually follows movement of the object; and using the image acquisition trigger rate, generating an image acquisition trigger signal and acquiring the image of the object.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

Figure 1:
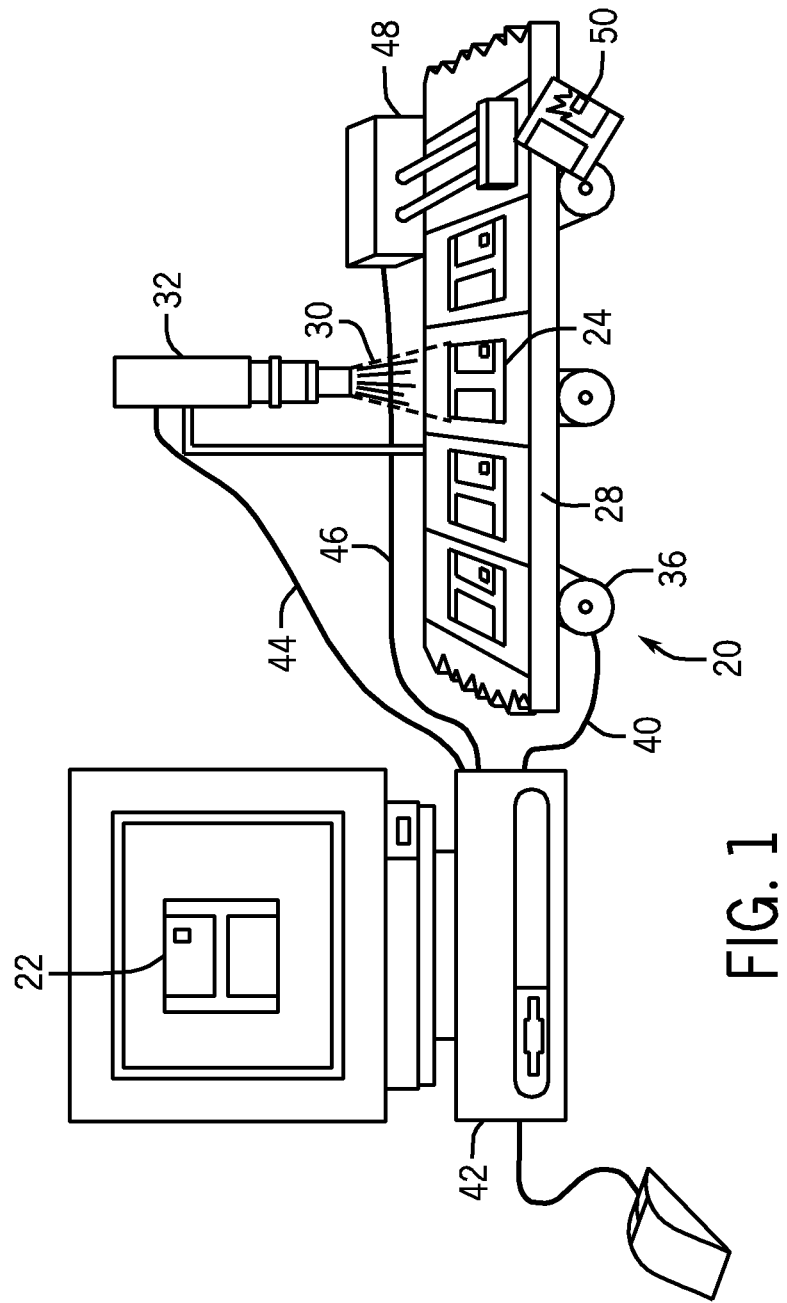
FIG. 1 is a schematic view of a typical vision system configuration including an encoder to provide encoder signals for calculating object position.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

The various aspects of the subject invention are now described with reference to the annexed drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to these configurations without departing from the scope or spirit of the claimed subject matter.

Embodiments of the invention are described below by using diagrams to illustrate either the structure or processing of embodiments used to implement the systems and methods of the present invention. Using the diagrams in this manner to present embodiments of the invention should not be construed as limiting of its scope. The present invention contemplates both systems and methods for calculating object position using data from a motion controller. The embodiments of the present invention may comprise a device, e.g., an automation device, a special purpose or general purpose computer including various computer hardware, software, and/or firmware, etc., as discussed in greater detail below.

The various embodiments of the invention will be described in connection with a machine vision system incorporating a smart camera configured to calculate an object's position using motion data from a motion controller. In some embodiments, the smart camera is configured to generate a virtual axis based on the motion data. That is because the features and advantages of the invention are well suited for this purpose. Still, it should be appreciated that the various aspects of the invention can be applied in other forms of imaging devices and in other systems that may have access to data from a motion controller.

An exemplary machine vision system may be used in a manufacturing assembly, test, measurement, automation, and/or control application, among others, as non-limiting examples. The exemplary machine vision system may use image acquisition software operable to perform any of various types of image acquisitions.

Figure 2:
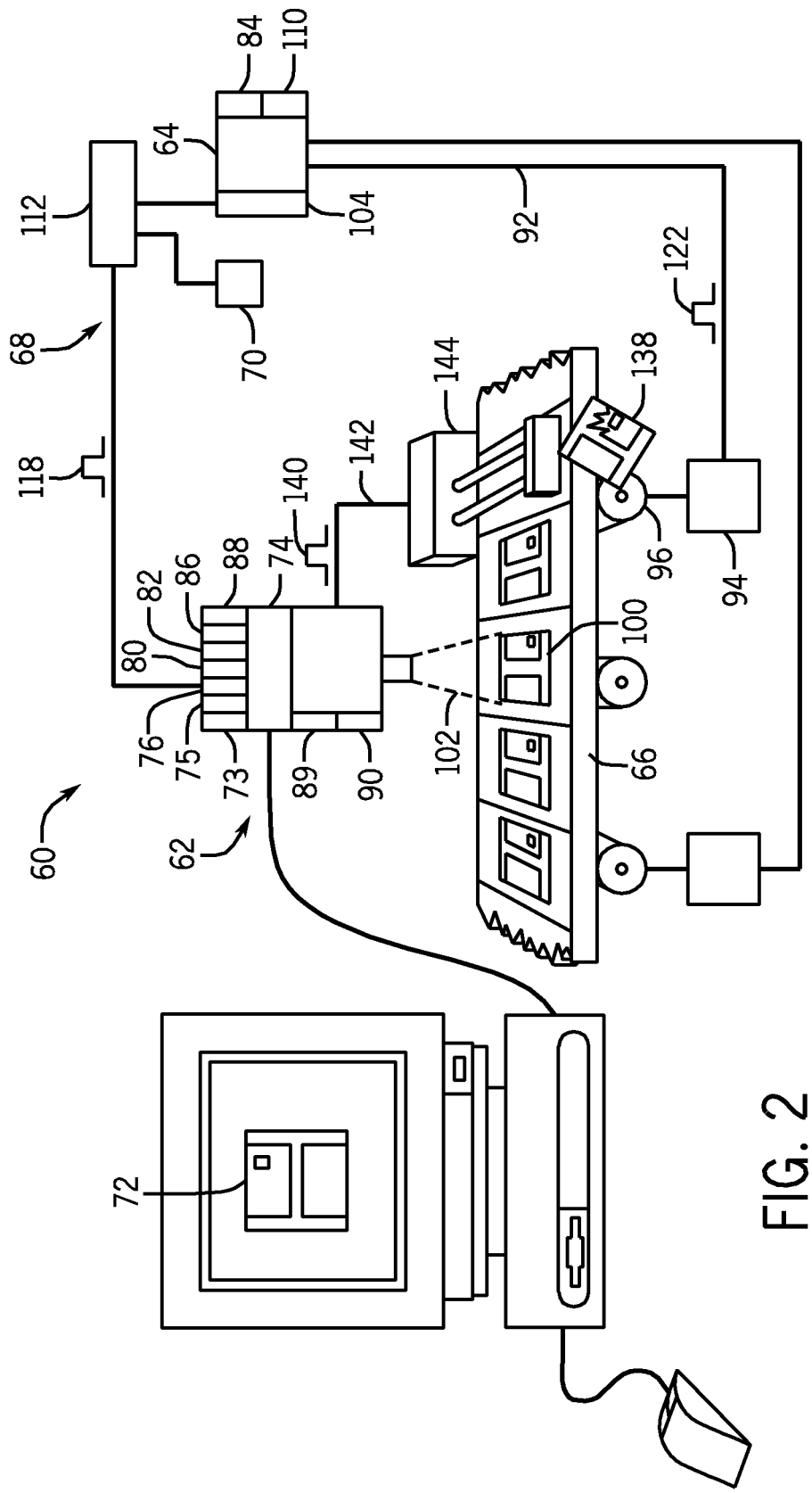
FIG. 2 is a schematic view of an exemplary vision system including a motion controller for providing motion data, the motion data used to generate a virtual axis, in accordance with the present embodiments.

Referring now to FIG. 2, an exemplary machine vision system 60 generally includes a smart camera 62, a motion controller 64 generally responsible for coordinating the movement of a movable system such as a robotic arm, a production line or conveyor 66, for example, and at least one communications network 68 to couple at least the smart camera 62 and the motion controller 64. In some embodiments, a dedicated master clock 70 may also be coupled to the network 68 to serve as a master time reference between devices on the network, including at least the smart camera 62 and the motion controller 64. In other embodiments, the motion controller 64 may serve as the master time reference. Each of these components will be described below in greater detail. It is to be appreciated that in other embodiments, one network, such as network 68 may be used for keeping devices on the network synchronized, while another network 78 may be used for the communication of motion data.

As used herein, the term "smart camera" is intended to include any of various types of image acquisition devices that are operable to acquire and/or store an image 72 and that includes on-board processing capabilities. A smart camera may thus be operable to acquire and analyze or process the acquired or stored image. Examples of a smart camera include analog and digital cameras, line scan cameras, infrared imaging devices, x-ray imaging devices, ultra-sonic imaging devices, and any other type of device which operates to receive, generate, process, or acquire an image or sensor data. The smart camera may be stationary in use, or the smart camera may be mobile and may be moving while acquiring an image.

The smart camera 62 of machine vision system 60 may include an acquisition controller 74 for performing an image acquisition function as described below. The acquisition controller 74 may include a processor 73 and memory 75 or a programmable hardware element, for example. The acquisition controller 74 may also include a network interface 76 to couple the smart camera to the network 68. The acquisition controller 74 may include a smart camera adjustable clock 80, and a smart camera synchronization application 82 that is capable of keeping the smart camera adjustable clock 80 synchronized with a motion controller adjustable clock 84 (discussed below) on the network 68.

The acquisition controller 74 may also include a virtual axis application 86. In some embodiments, the virtual axis application generates a virtual axis 88 in memory 75 that can be controlled by the motion controller 64. In other embodiments, the motion controller 64 may provide motion data to the acquisition controller 74 that can be used to enable the virtual axis application 86. It is to be appreciated that components described as being a part of the acquisition controller 74 are also considered as part of the smart camera 62, and components described as being a part of the smart camera 62 are also considered as part of the acquisition controller 74.

The smart camera 62 may also include a processor 89 and a memory medium 90 on which computer programs may be stored and/or executed. In other embodiments, configuration information may be stored that may be used to configure a programmable hardware element, such as a field programmable gate array (FPGA), comprised in the smart camera to perform a calculation, measurement, control, automation, or analysis function, among others.

As used herein, the terms "memory" and "memory medium" includes a non-volatile medium, e.g., a magnetic media or hard disk, optical storage, or flash memory; a volatile medium, such as computer system memory, e.g., random access memory (RAM) such as DRAM, SRAM, EDO RAM, RAMBUS RAM, DR DRAM, etc.; or an installation medium, e.g., a CD-ROM, or floppy disks, on which the computer programs may be stored.

Motion of the conveyer 66 may be controlled by the motion controller 64, or more than one motion controller. The motion controller 64 sends position signals over a link 92 to control operation of a motion drive, such as servo drive 94 coupled to a servo motor 96, which in turn controls the motion of the conveyor 66. In some embodiments, the link 92 may be coupled to a network hub 112 (discussed further below) instead of directly to the motion controller. The motion controller 64 or the dedicated master clock 70, for example, may provide the common time reference for the servo drive 94.

In the exemplary vision system 60, more than one servo drive and motor may be used. Accordingly, the motion controller 64 may be responsible for coordinating the movement of the servo motor 96 on the conveyor so the conveyor 66 is able to transport one or more objects 100 to cause relative movement between the objects 100 and the field of view 102 of the smart camera 62.

Similar to the acquisition controller 74, or smart camera 62, the motion controller 64 may also include a network interface 104 to couple the motion controller to the network 68. The motion controller 64 may also include the motion controller adjustable clock 84, and a motion controller synchronization application 110 that is operable for keeping the motion controller adjustable clock 84 synchronized with the smart camera adjustable clock 80 across the network 68.

The smart camera 62 and the motion controller 64 are both coupled to the communications network 68. One example of a common communications network is a non-deterministic network, such as an Ethernet based network. Another example is a deterministic, low-latency network, such as an EtherCAT or PowerLink based network. Other possible communication networks would also be known to one skilled in the art. In this embodiment, a network hub 112 may be used to serve as a common connection point for the smart camera 62 and the motion controller 64 on the network 68.

As mentioned above, in some embodiments, a dedicated master clock 70 may also be coupled to the network 68. When used, the master clock 70 may serve as the dedicated clock between the devices on the network 68, either independent of or in conjunction with the smart camera adjustable clock 80 and the motion controller adjustable clock 84. The smart camera synchronization application 82 and the motion controller synchronization application 110 may also be capable of keeping the smart camera adjustable clock 80 and the motion controller adjustable clock 84 synchronized with the master clock 70 across the network 68.

Algorithms used to synchronize local clocks between devices on a non-deterministic network are described by the IEEE-1588 standard, which is incorporated herein by reference. Algorithms used to convert target position, velocity, and/or acceleration into a motion curve are documented under the ODVA CIP specification, which is also incorporated herein by reference. It is to be appreciated that one of skill in the art would understand the workings of both the IEEE-1588 standard and the ODVA CIP specification.

Figure 3:
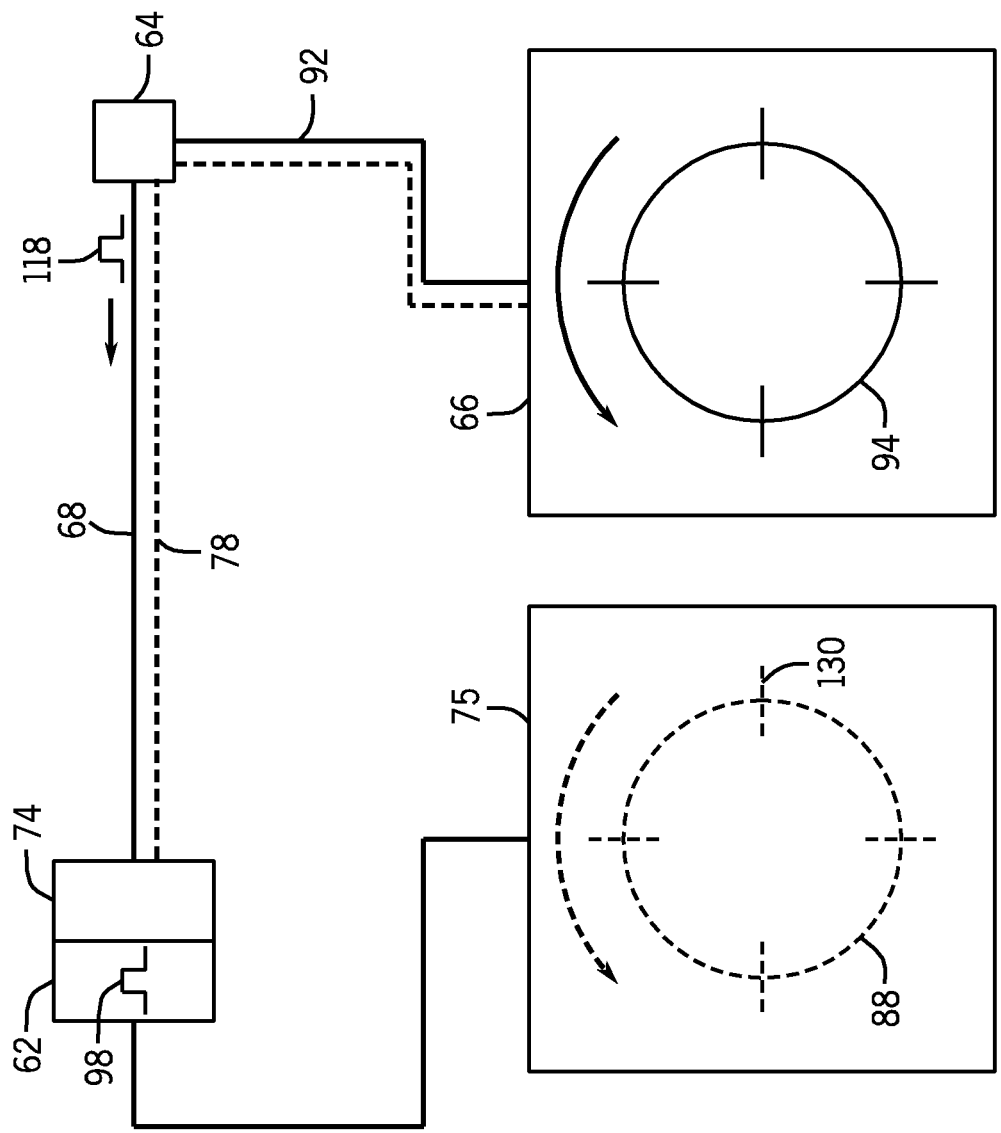
FIG. 3 is a schematic view, showing various vision system signals, and a virtual axis tracking a motion drive.

Referring to FIGS. 2 and 3, the motion controller 64 can send motion data 118 over the network 68 to the smart camera 62, in some embodiments via the acquisition controller 74, which uses the virtual axis application 86 in conjunction with the motion data to calculate object 100 position, and to generate a trigger signal 98 at calculated times for the smart camera 62 to acquire one or more images of the object 100 in the field of view 102.

As described above, the smart camera 62 and the motion controller 64 may utilize the smart camera synchronization application 82 and the motion controller synchronization application 110, respectively, along with the smart camera adjustable clock 80 and the motion controller adjustable clock 84, and/or the dedicated master clock 70, to generate a synchronized clock so as to create a common time reference between the smart camera 62 and the motion controller 64. This common time reference between the smart camera 62 and the motion controller 64 may be within about 10 usec., although more or less is contemplated.

At a frequency of between about 50 Hz to about 2500 Hz, or more or less, the motion controller 64 communicates motion data 122 to the servo drive 94. The motion data 122 may include a variety of parameters including a target position, target velocity, velocity limits, target acceleration, acceleration limits, and/or a time at which the target should reach a target position and/or velocity. Motion data may also include other data parameters, some of which are described by the IEC 61800-7 standard, which is incorporated herein by reference. The motion controller 64 may also transmit motion data to the smart camera 62 over the network 68, or a separate network. The time may be implied rather than transmitted, such as where nodes, e.g., devices, on the network are synchronized by fixed cycles on the network, and implicitly any command takes effect on the start of a subsequent motion cycle.

For every motion cycle, in some embodiments, the motion controller 64 determines the motion data for the next motion cycle, and communicates the motion data for the next motion cycle to the smart camera 62 in a message 124. The smart camera 62, upon receiving the message 124, may use the virtual axis application 86 to plan the movement of a virtual axis 88 for the next motion cycle. One of skill in the art would recognize that different motion networks and different motion controllers may have differing rules for how the motion data is defined, how the motion data is transmitted on the network, and how movement of an axis is determined from the motion data.

Based on the motion data, the virtual axis 88 is generated by the virtual axis application 86. The virtual axis 88 serves to move in a fixed relationship to the servo drive 94. In some embodiments, the motion controller "gears" the virtual axis 88 based on the servo drive axis such that when the virtual axis reaches a certain position, the object 100 is in the field of view 102 of the smart camera 62, and an image acquisition can be triggered. In other embodiments, the motion controller 64 may indicate to the smart camera 62 the position of the virtual axis 88 when the object 100 will be in the field of view 102. This may be based on other sensors connected to the motion controller 64 detecting the position of the object on the conveyor 66. From the virtual axis 88, a user-specified multiplier 130 may be used to generate an image acquisition trigger rate 132 that virtually follows the movement of the object 100 on the conveyor 66. For example, one revolution of the virtual axis may define one part cycle as is seen by the camera 62, and the camera may want to acquire three images of the part, a user could specify that the acquisition trigger is to be signaled every 120 degrees. Similarly, for a line scan camera, a user may want to acquire a single line every 0.5 degrees in order to acquire exactly 720 lines of the part.

Based on the calculated image acquisition trigger rate 132, the smart camera 62 generates the image acquisition trigger signal 98 at a frequency relative to the object movement commanded by the motion controller 64 to the servo drive 94. Because the smart camera 62, motion controller 64, and servo drive 94 are all synchronized by a common time base, the smart camera 62 may be able to generate the image acquisition trigger signal 98 that is close, within acceptable limits, to the actual object movement without the use of a hardware encoder.

In some embodiments, the machine vision system 60 may be configured to detect a defective object 138. When an object is defective, the smart camera 62 and/or the motion controller 64 may be programmed to send a fail signal 140 over link 142 to a reject actuator 144 to remove the object 138 from the conveyor 66. The fail signal 140 can be generated by the time the object to be rejected arrives at the reject actuator 144 farther down the conveyor from the smart camera 62. In order to generate the fail signal 140 in the presence of conveyor speed changes, the smart camera 62 can determine how fast the conveyor 66 is moving. The smart camera 62 synchronized to the motion controller 64 as described above would be able to precisely generate the fail signal 140 when the object arrived at the reject actuator 144 regardless of line speed. This configuration may be applied to any output from the smart camera 62 that may be synchronized with conveyor movement.

The components of the exemplary machine vision system 60 described above are configured such that the smart camera 62 is able to coordinate the generation of an image acquisition trigger with the motion of the object 100 being inspected on the conveyor 66, based on motion data from the motion controller, and without the smart camera 62 sending any motion data to the motion controller.

Figure 4:
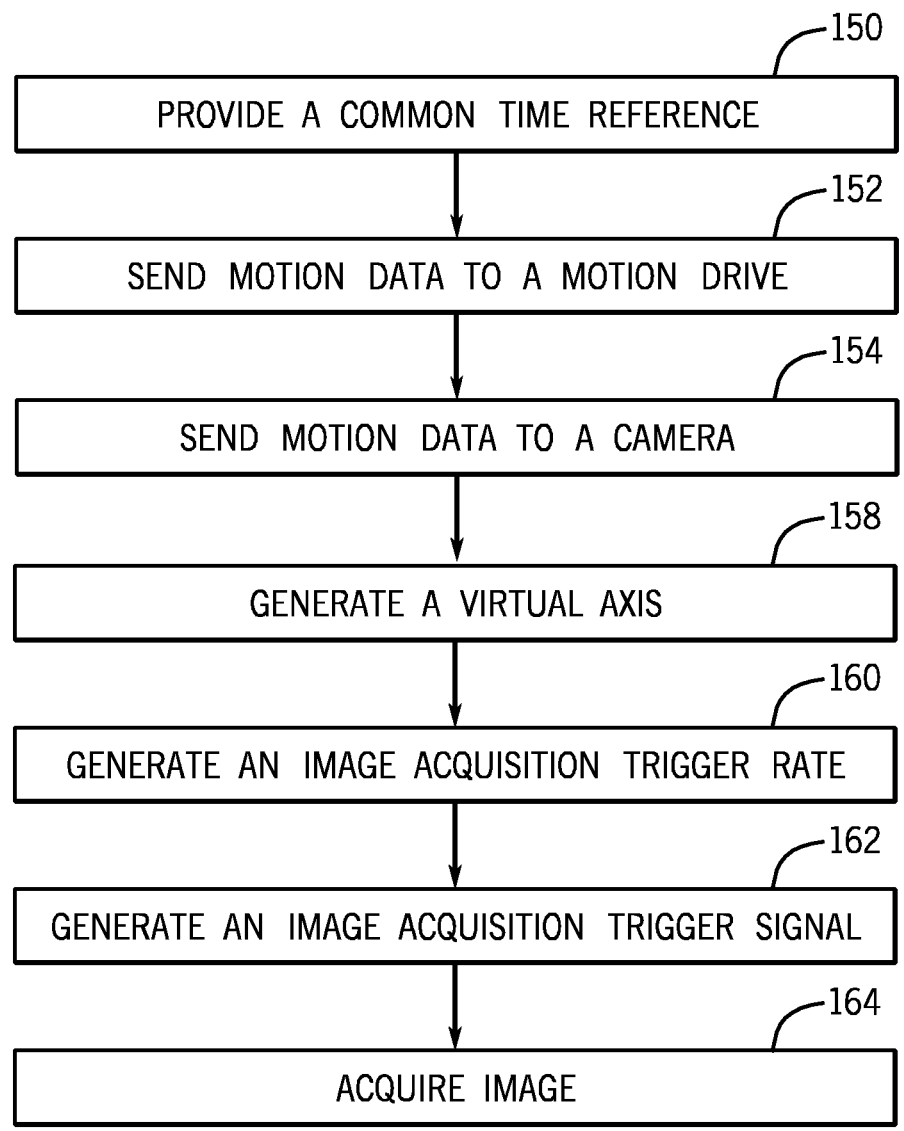
FIG. 4 is a flow chart of a method in accordance with the present embodiments.

FIG. 4 illustrates an embodiment of a method for triggering line acquisitions of a smart camera using servo motor motion data communicated from a networked motion controller for acquiring an image of the object. The method shown in FIG. 4 may be used in conjunction with any of the systems or devices shown in the above Figures, among others. In various embodiments, some of the method elements shown may be performed concurrently, in a different order than shown, or may be omitted. Additional method elements may also be performed as desired.

Referring to FIG. 4, a method is shown for acquiring an image of an object. A first step is to provide a common time reference to the smart camera 62 and the motion controller 64, as indicated at process block 150. As previously described, the smart camera and the motion controller can be in communication via the network 68. At process block 152, the motion controller sends a motion data signal to a motion drive. The motion data signal may be sent over link 92, or across the network 68, for example. At process block 154, the motion controller sends the motion data over the network 68 to the smart camera 62. Upon receiving the motion data, the smart camera 62 uses the virtual axis application 86 on the smart camera 62 to generate a virtual axis 88 in memory 75 from the motion data, with the virtual axis 88 moving in a generally fixed relationship to the motion drive 94, as indicated at process block 158. Using the virtual axis 88, an image acquisition trigger rate can be generated that virtually follows relative movement of the object 100, as indicated at process block 160. Using the image acquisition trigger rate, an image acquisition trigger signal can be generated, at process block 162, and the smart camera may acquire an image of the object 100, as indicated at process block 164. The image acquisition trigger signal may be generated at a frequency relative to the object movement commanded by the motion controller.

Although the present invention has been described with reference to preferred embodiments, workers skilled in the art will recognize that changes may be made in form and detail without departing from the spirit and scope of the invention. For example, the present invention is not limited to the embodiments of smart cameras and associated devices shown herein and may be practiced with other image acquisition devices.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A vision system for triggering an image acquisition of an object using motion data communicated from a motion controller on a network, the motion controller coupled to a motion drive, the system comprising:
   a camera;
   an acquisition controller coupled to the camera, the acquisition controller including a network interface, the network interface operable to couple to the network;
   wherein the camera, upon receiving motion data from the motion controller, uses a virtual axis application to plan the movement of a virtual axis for a motion cycle, the virtual axis allowing an acquisition trigger rate to be calculated by the camera that follows movement of the object caused by the motion drive; and
   wherein, based on the calculated acquisition trigger rate, the camera generates an acquisition trigger signal for triggering the image acquisition of the object.

2. The vision system according to claim 1,
   further including a camera clock synchronization application operable to synchronize with a common time reference for the synchronization of motion commands; and
   wherein the common time reference is provided by at least one of the motion controller, a camera clock, a dedicated master clock, and the motion drive.

3. The vision system according to claim 1,
   wherein the network is a non-deterministic network.

4. The vision system according to claim 1,
   wherein the network is a deterministic, low-latency network.

5. The vision system according to claim 2,
wherein the camera clock synchronization application and a motion controller clock synchronization application are operable to interface with the common time reference, and both the camera clock synchronization application and the motion controller clock synchronization application are responsible to keep a camera clock and a motion controller clock synchronized.

6. The vision system according to claim 1,
wherein the virtual axis is generated by a virtual axis application.

7. The vision system according to claim 1,
wherein a user-specified multiplier is used with the virtual axis to generate the acquisition trigger rate.

8. The vision system according to claim 1,
wherein the camera generates the acquisition trigger signal at a frequency relative to the movement of the virtual axis based on the motion data from the motion controller.

9. The vision system according to claim 2,
wherein the common time reference synchronizes the motion commands between the motion controller, the motion drive, and the camera.

10. The vision system according to claim 2,
wherein the IEEE-1588 standard is used to synchronize the motion commands.

11. The vision system according to claim 2,
wherein network cycles occurring at a fixed frequency are used to synchronize the motion commands.

12. The vision system according to claim 2,
wherein both the IEEE-1588 standard and network cycles occurring at a fixed frequency are used in combination to synchronize the motion commands.

13. A vision system comprising:
a camera, the camera operable to trigger an image acquisition of an object using motion data communicated from a motion controller on a network, the motion controller coupled to a motion drive;
the camera including a virtual axis application and an acquisition controller, the acquisition controller coupleable to the network;
a common time reference provided by at least one of the motion controller, a camera clock, a dedicated master clock, and the motion drive;
wherein the camera, upon receiving the motion data communicated from the motion controller, uses a virtual axis application to plan the movement of a virtual axis for a motion cycle, the virtual axis operable to follow relative movement of the object caused by the motion drive; and
wherein, based on movement of the virtual axis, the camera generates an acquisition trigger signal for triggering the image acquisition of the object.

14. The vision system according to claim 13,
wherein the motion controller gears the virtual axis based on an axis of the motion drive such that when the virtual axis reaches a certain position, the object is in a field of view of the camera, and the image acquisition is triggered.

15. The vision system according to claim 13,
wherein the motion controller indicates to the camera the position of the virtual axis when the object is in the field of view of the camera.

16. The vision system according to claim 13,
wherein the virtual axis moves in a fixed relationship to the motion drive.

17. A method for acquiring an image of an object, the method comprising:
providing a common time reference to a camera and a motion controller, the camera and the motion controller being in communication on a network;
the motion controller sending motion data to a motion drive;
the motion controller sending the motion data over the network to the camera;
upon receiving the motion data, the camera planning the movement of a virtual axis, the virtual axis moving in a fixed relationship to the motion drive;
using the virtual axis, generating an image acquisition trigger rate that virtually follows movement of the object;
using the image acquisition trigger rate, generating an image acquisition trigger signal; and
acquiring the image of the object.

18. The method according to claim 17,
further including generating the image acquisition trigger signal at a frequency relative to the virtual axis based on the motion data from the motion controller.

19. The method according to claim 17,
further including coordinating movement of a servo motor on a conveyor, the servo motor coupled to the motion drive, so the conveyor transports the object to cause relative movement between the object and a field of view of the camera.

20. The method according to claim 17,
further including gearing the virtual axis based on an axis of the motion drive such that when the virtual axis reaches a certain position, the object is in a field of view of the camera; and
triggering an image acquisition.

21. The method according to claim 17,
further including indicating to the camera the position of the virtual axis when the object will be in a field of view of the camera.

22. The method according to claim 17,
wherein the motion data includes at least one of a target position, target velocity, velocity limits, target acceleration, acceleration limits, and a time at which the target should reach at least one of a target position and velocity.

23. The method according to claim 22,
further including implying the time by using fixed cycles on the network, such that commands take effect on the start of a next fixed cycle.

24. The method according to claim 17,
further including coordinating movement of a servo motor on a movable system, the servo motor coupled to the motion drive, so the movable system transports the camera to cause relative movement between the object and a field of view of the camera.

* * * * *